United States Patent [19]
Terayama et al.

[11] 4,440,788
[45] Apr. 3, 1984

[54] CYSTEINE DERIVATIVES

[75] Inventors: Hiroshi Terayama, Tokyo; Yoshiharu Morita; Kohei Umezu, both of Yokohama, all of Japan

[73] Assignee: Mitsubishi Chemical Industries, Limited, Tokyo, Japan

[21] Appl. No.: 336,377

[22] PCT Filed: May 11, 1981

[86] PCT No.: PCT/JP81/00107
§ 371 Date: Dec. 30, 1981
§ 102(e) Date: Dec. 30, 1981

[87] PCT Pub. No.: WO81/03330
PCT Pub. Date: Nov. 26, 1981

[30] Foreign Application Priority Data

May 13, 1980 [JP] Japan ................................ 55-63263
Jun. 27, 1980 [JP] Japan ................................ 55-87272

[51] Int. Cl.³ .................... A61K 31/16; C07C 149/23; C07C 103/183

[52] U.S. Cl. ..................................... 424/320; 564/154; 564/151; 564/197; 564/198; 260/500.5 H; 546/245; 548/188; 548/540

[58] Field of Search .......................... 564/154; 424/320

[56] References Cited

U.S. PATENT DOCUMENTS 2,940,933  6/1960  Jezl ................................ 564/154 X
3,340,147  9/1967  Martin et al. .................... 564/154 X
4,216,225  8/1980  Shiratsuchi et al. ............. 564/154 X

FOREIGN PATENT DOCUMENTS 668235  3/1952  United Kingdom ................ 564/154
420167  8/1974  U.S.S.R. ............................ 564/154

Primary Examiner—Thomas A. Waltz
Attorney, Agent, or Firm—Oblon, Fisher, Spivak, McClelland & Maier

[57] ABSTRACT

This invention relates to S-alkylcysteines and processes for preparing same. The compounds according to this invention are expected to be applicable as therapeutic agents for hepatic failures.

3 Claims, No Drawings

CYSTEINE DERIVATIVES

TECHNICAL FIELD

This invention relates to cysteine derivatives useful as therapeutic agents for hepatic failures and a process for preparing same.

BACKGROUND ART

The liver is the single organ that is largest in the body and is said to have more than one hundred different kinds of functions including, in addition to metabolism of carbohydrates, lipids, proteins and amino acids, bile production, detoxication, foreign matter treatment, control of hormones, production of prothrombin, one of blood coagulating agents, storage of various constituents of organisms (such as fat, glycogen, proteins, vitamines, etc.) and the like. This organ which has such precise and well-balanced functions possesses a large self-restorative ability and hence is expected to heal spontaneously even if it is functionally disordered. Nevertheless the liver may suffer an acute or chronic lesion due to one or more of various factors such as alcohol, undernutrition, virus infection, medicaments, poisons, biliary obstruction, disorder of the enterohepatic circulatory system and the like and such lesion is manifested as one or more of diseases such as fatty liver, drug-toxic hepatic failure, drug-hypersensitive hepatic failure, alcoholic hepatitis, viral hepatitis, congestive hepatitis, hepatopathy due to biliary engorgement, jaundice, and hepatocirrhosis which is the final picture of the foregoing diseases.

When these hepatic failures are induced, a medication can be employed with the intention of accelerating restoration of cells of the liver parenchyma or alleviating the damage of liver cells with the aid of protection against various hepatopathy-inducing factors, thereby accelerating the recovery from its functional disorder or preventing aggravation.

The inventors have found that paticular cysteine derivatives are effective for the above-mentioned purpose and accomplished the present invention.

DISCLOSURE OF INVENTION

In brief, the present invention resides in
(1) a cysteine derivative of the formula:

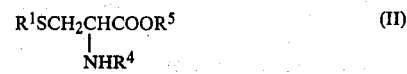

wherein $R^1$ is methyl or ethyl, $R^2$ and $R^3$ are each hydrogen or a lower alkyl having 1 to 6 carbon atoms, or one of $R^2$ and $R^3$ is amino, monomethylamino, dimethylamino or hydroxyl and the other is hydrogen or a lower alkyl having 1 to 6 carbon atoms, or $R^2$ and $R^3$, taken together, may stand for an alkylene chain or a hetero-atom containing alkylene chain, thereby forming a ring along with the nitrogen atom, and $R^4$ is hydrogen or acetyl;

(2) a process for preparing a cysteine derivative of the foregoing formula (I) which comprises reacting a cysteine alkyl ester of the formula:

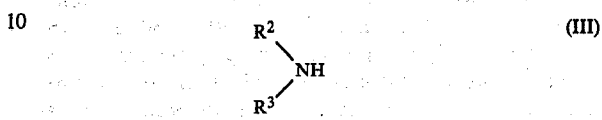

wherein $R^1$ and $R^4$ are as defined in formula (I) and $R^5$ is methyl or ethyl, with an amino compound of the formula:

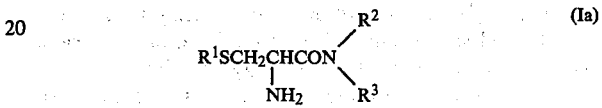

wherein $R^2$ and $R^3$ are as defined in formula (I);

(3) a process for preparing a cysteine derivative of the formula:

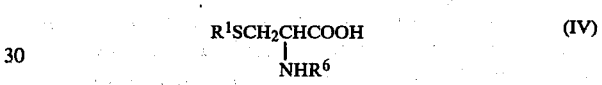

wherein $R^1$, $R^2$ and $R^3$ are as defined in formula (I), which comprises reacting an S-alkyl-cysteine of the formula:

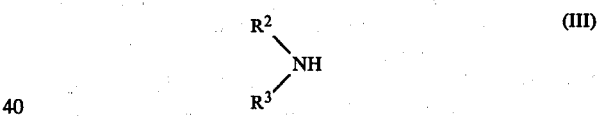

wherein $R^1$ is as defined in formula (I) and $R^6$ is an amino-protecting group, or its reactive derivative with an amino compound of the formula:

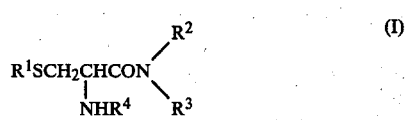

wherein $R^2$ and $R^3$ are as defined in formula (I), then eliminating the amino-protecting group, if necessary, followed by neutralization; and (4) a process for preparing a cysteine derivative of the foregoing formula (I) which comprises reacting an S-alkyl-N-acetyl-cysteine of the formula:

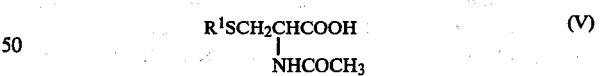

wherein $R^1$ is as defined in formula (I), or its reactive derivative with an amino compound of the foregoing formula (III).

Now the present invention is described in detail.

The compounds according to this invention are cysteine derivatives of the foregoing formula (I).

In formula (I), $R^1$ is methyl or ethyl and $R^2$ and $R^3$ are each hydrogen or a lower alkyl having 1 to 6 carbon atoms such as methyl, ethyl, propyl, butyl, pentyl, hexyl or the like, or one of $R^2$ and $R^3$ is amino, monomethylamino, dimethylamino or hydroxyl and the other is hydrogen or a lower alkyl having 1 to 6 carbon atoms, or $R^2$ and $R^3$ taken together stand for an alkylene chain such as tetramethylene or pentamethylene or an alkylene chain containing at least one hetero-atom such as sulfur, nitrogen or oxygen atom. Illustrative of such hetero-atom containing alkylene chain are 2-thia-tetramethylene, 3-aza-pentamethylene, 3-oxa-pentamethylene and the like. $R^1$, $R^2$ and $R^3$ may be the same or different from one another.

The cysteine derivatives of formula (I) include, for example, the following compounds.

(i) S-Alkylcysteinamides:

S-methylcysteinamide, S-methylcysteine methylamide, S-methylcysteine ethylamide, S-ethylcysteine dimethylamide, N-(S-methylcysteinyl)-azetidine, N-(S-methylcysteinyl)pyrrolidine, S-ethylcysteinamide, S-ethylcysteine methylamide, S-ethylcysteine ethylamide, S-ethylcysteine propylamide, S-ethylcysteine butylamide, S-ethylcysteine pentylamide, S-ethylcysteine hexylamide, S-ethylcysteine dimethylamide, S-ethylcysteine methylethylamide, S-ethylcysteine diethylamide, N-(S-ethylcysteinyl)-azetidine, N-(S-ethylcysteinyl)-pyrrolidine, N-(S-ethylcysteinyl)-piperidine, etc.

These S-alkylcysteinamides may be used in the form of salts, which includes, for example, non-toxic salts with an inorganic acid such as hydrochloric acid or sulfuric acid or an organic acid such as maleic acid, fumaric acid or succinic acid.

(ii) S-Alkyl-N-acetyl-cysteinamides: S-methyl-N-acetyl-cysteinamide, S-methyl-N-acetyl-cysteine methylamide, S-methyl-N-acetyl-cysteine ethylamide, S-methyl-N-acetyl-cysteine propylamide, S-methyl-N-acetyl-cysteine butylamide, N-(S-methyl-N-acetyl-cysteinyl)pyrrodiline, N-(S-methyl-N-acetyl-cysteinyl)-thiazolidine, S-ethyl-N-acetyl-cysteinamide, S-ethyl-N-acetyl-cysteine methylamide, S-ethyl-N-acetyl-cysteine ethylamide, S-ethyl-N-acetyl-cysteine propylamide, S-ethyl-N-acetyl-cysteine butylamide, N-(S-ethyl-N-acetyl-cysteinyl)pyrrolidine and N-(S-ethyl-N-acetyl-cysteinyl)-thiazolidine, S-methyl-N-acetylcysteinylhydrazine, N-methyl-N-(S-methyl-N-acetylcysteinyl)hydrazine, N-(S-methyl-N-acetylcysteinyl)-N'-methylhydrazine, N-methyl-N-(S-methyl-N-acetylcysteinyl)-N'-methylhydrazine, N-(S-methyl-N-acetylcysteinyl)-N',N'-dimethylhydrazine, N-(S-methyl-N-acetylcysteinyl)-hydroxylamine, N-methyl-N-(S-methyl-N-acetylcysteinyl)-hydroxylamine.

These compounds may be present in the form of D-, L- or DL-isomers and usually their L- or DL-isomers are used.

The inventors have found that the compounds of the above formula (I) has the advantage of activation of liver cells, thereby activating various functions of the liver such as carbohydrate metabolism, detoxication (such as alcohol detoxication), formation and secretion of bile and bile acids (cholekinetic action) and the like.

Also the inventors have found that the compounds of the above formula (I) possess a pharmacological activity by working on an already disordered liver so as to alleviate or eliminate the disorder.

Furthermore, the inventors have found that the compounds of the above formula (I) possess another pharmacological activity of protecting liver functions against a certain disorder or load.

Toxic hepatopathy, hepatitis or fatty liver is induced by various causes and its primary lesion is necrosis of liver cells, reaction in the interstial system or retention of fat.

The feature of necrosis depends on its cause and may be divided into centrolobular, perilobular and sporadolobular necrosis.

Symptomatic models of these lesions can be produced experimentally by applying the following chemical to a test animal.

Centrolobular necrosis can be induced with carbon tetrachloride, thioacetamide, chloroform or bromobenzene.

Perilobular necrosis can be induced with allyl alcohol.

Sporadolobular necrosis which is accompanied by a reaction in the interlobar system can be induced with D-galactosamine.

A symptomatic model of fatty liver can be produced with carbon tetrachloride or ethionine.

It is known that these acute, subacute or chronic disorders of the liver lead to liver cirrhosis as the final picture, and a symptomatic model of liver cirrhosis can be produced experimentally, for example, by repeated administration of carbon tetrachloride to a test animal for a prolonged period of time.

It has been found during the preparation of hepatitis in test animals that the compounds according to this invention exert their beneficial effects through stabilization of cell membranes, radical elimination effect, protection of in vivo thiol compounds due to anti-oxidation effect, and activation of various intrahepatic enzymes by the nature of thiol compounds.

For instance, the following effects are noted:

(1) therapeutic effect (the term "therapy" used herein being intended to include both prevention and amelioration) on hepatopathy which accompanies centrolobular necrosis;

(2) therapeutic effect on hepatopathy accompanied by perilobular necrosis;

(3) therapeutic effect on hepatitis accompanied by sporadolobular necrosis and reaction in the interlobar system;

(4) therapeutic effect on fatty liver;

(5) therapeutic effect on hepatocirrhosis (liver cirrhosis);

(6) therapeutic effect on toxic hepatopathy;

(7) therapeutic effect on congestive liver;

(8) accelerative effect on secretion of bile and bile acids (cholekinetic effect);

(9) ameliorative effect on poisoning reactions by metal salts (selenium salts and cadmium salts); and so on.

Thus, the compounds of this invention serve as liver function recovering or stimulating agents with the intention of accelerating the regeneration or new generation of parenchymatous cells of the liver when the number or function of the cells is reduced due to hepatic failure such as acute or chronic hepatitis, etc., or poisoning by a chemical, and hence they are valuable as therapeutic agents for hepatic failures in human being and animals.

Thus, according to the present invention, the compounds of formula (I) can be used as therapeutic agents for fatty liver, alcoholic hepatitis, hepatitis, toxic hepatopathy, congestive liver, biliary engorgement-induced hepatopathy, or liver cirrhosis that is the final picture of these diseases.

According to histopathological findings, the compounds of this invention have therapeutic effects on those liver disorders which are caused by centrolobular necrosis or perilobular necrosis of the liver or sporadolobular necrosis thereof which involves a reaction in the interlober system. Therefore, they are useful as therapeutic agents for hepatic failures accompanied by such necrosis.

Since the compounds of this invention also exert their effect in activating liver cells and thereby activating such functions of the liver as secretion of bile and bile acids, carbohydrate metabolism, detoxication of hepatotoxic substances including alcohol in the liver, they are useful as cholekinetic agents or therapeutic agents for jaundice in human being and animals.

In application of the compounds of this invention as therapeutic agents for hepatic failures, they may be used in any form which is suited to attain the desired beneficial effect. The compounds of this invention may be used as therapeutic agents for hepatic failures as they are. Also they may be formulated with a pharmaceutically acceptable carrier or diluent or with another pharmacologically active substance according to the conventional manner in pharmaceutics.

Pharmaceutical compositions comprising a compound of this invention (hereinafter referred to as "pharmaceutical composition of this invention") may be provided in the form of dosage unit.

The pharmaceutical compositions of this invention may be applied orally or parenterally. The oral administration includes sublingual administration.

The form in which the pharmaceutical compositions of this invention may be provided includes powders, granules, tablets, sugar-coated tablets, pills, capsules, solutions, etc. for oral administration, as well as suppositories, suspensions, solutions, emulsions, ampules, injections, etc. for parenteral administration. Of course, a combination of these may be employed.

The pharmaceutical compositions of this invention generally comprises 0.01 to 100% by weight of a compound or compounds of this invention.

The carriers which may be formulated with the compounds of this invention may be any of solid, semisolid and liquid and include, for example, excipients, extenders, binders, wetting agents, disintegrating agents, surfactants, lubricants, dispersing agents, buffers, corrigents, aromatics, coloring agents, perfumes, preservatives, dissolution aids, solvents, coating agents, sugar coating agents and capsules. Of course, two or more of these carriers may be used in combination. The diluents include, for example, water; gelatine; saccharides such as lactose and glucose, starches such as corn, wheat, rice, arrowroot and potate starches; fatty acids such as stearic acid; fatty acid salts such as calcium stearate and magnesium stearate; talc; vegetable oils; alcohols such as stearyl alcohol, benzyl alcohol and polyalkylene glycol; gums; oils such as petroleum and mineral oil; physiological saline; dextrose or similar saccharide solutions and the like.

The pharmaceutical compositions of this invention may be prepared in a conventional manner. For instance, a compound of this invention may be admixed with a carrier to make granules and the resulting composition is admixed with another carrier to form tablets. Likewise granulation or powder packaging may be employed. These capsules, tablets, granules and powders generally comprises 5% to 100%, preferably 25% to 100% by weight of a compound or compounds of this invention.

Solutions for oral administration may preferably be in the form of suspensions or syrups which contain 0.5% to 10% by weight of a composition of this invention.

Parenteral solutions are usually made aseptic and, if necessary, isotonic with blood.

Suitable vehicles for injection include sterilized water, lidocaine hydrochloride solutions (for intramuscular injection), physiological saline, glucose, liquids for intravenous injection and electrolyte solutions (for intravenous injection and drip infusion). These injections may usually be prepared so as to contain 0.5% to 20%, preferably 1% to 10% by weight of a compound of this invention.

The dose of a pharmaceutical composition of this invention is decided by a physician by considering the species to be treated (whether a human being or an animal), age, sex, weight and sensitivity of the patient, route, time and interval of administration, degree of the hepatopathological condition, health condition, nature, formulation and type of the pharmaceutical composition, type of the active ingredient, and the like.

In order to obtain beneficial results with animals, it is advantageous to apply a dose of the active ingredient in the range of 0.1 to 500, preferably 1 to 100 mg/kg-body weight/day for oral administration and a dose thereof in the range of 0.01 to 250, preferably 0.1 to 25 mg/kg-body weight/day for parenteral administration.

In order to obtain beneficial results with human being, for example, the following dose range is considered advantageous from the effective dose range with animals taking into account the sensitivity difference, safety and the like: 0.1 to 250, preferably 0.5 to 50 mg/kg-body weight/day for oral administration and 0.01 to 100, preferably 0.1 to 25 mg/kg-body weight/day for parenteral administration.

Of course, depending to the above-mentioned conditions, a dose less than the lower limit of the above range may be applied successfully or it might be necessary to apply a dose which exceeds the upper limit of the above range.

In the case of large doses, they are preferably administered in several times a day.

The compounds (I) according to the present invention may be prepared, for example, by the above-mentioned processes, which are described below more fully.

(I) S-Alkylcysteinamides

In the S-alkylcysteines of Formula (IV), $R^6$ is a protective group for amino such as, for example, t-butyloxycarbonyl, t-amyloxycarbonyl, benzyloxycarbonyl or para-substituted benzyloxycarbonyl (e.g., p-nitrobenzyloxycarbonyl, p-methoxybenzyloxycarbonyl). The amino-protecting group is preferably such that can be readily eliminated with an acid (e.g., hydrogen chloride, hydrogen bromide). Since the compounds according to this invention are sulfur-containing amino acids, those amino-protecting groups which are eliminated by means of catalytic hydrogenation are not preferred.

The reactive derivatives of the S-alkylcysteines include, for example, mixed acid anhydrides such as mixed anhydrides with an alkyl carbonate, acid chlorides, etc. It is not always necessary to isolate and purify these reactive derivatives. For example, an S-alkylcysteine of formula (IV) is reacted with an alkyl chloroformate or thionyl chloride and the resulting alkyl carbonate mixed anhydride or acid chloride may be used without isolation and purification.

In the reaction of an S-alkylcysteine of formula (IV) and an amino compound of formula (III), the latter is usually used in excess.

The reaction is usually carried out at room temperature or under cooling in the presence of a base such as triethylamine, dimethylaniline, etc. in an organic solvent such as acetone, tetrahydrofuran, dioxane, dimethylformamide, chloroform, dichloromethane or hexamethylphosphoramide, a mixture of two or more of these solvents or a mixture of water with one or more of these organic solvents.

After the reaction, the amino-protecting group is eliminated in a conventional manner and, if necessary, the product is neutralized with an acid as mentioned above to give the desired product.

Similarly, in the reaction of an S-alkylcysteine of formula (II) (R$^4$: H) with an amino compound of formula (III), the latter is usually used in excess.

The reaction is usually carried out at room temperature or under cooling in an organic solvent or without solvent.

After the reaction, if necessary, an acid as mentioned above may be added to neutralize, thereby providing the desired compound.

(II) S-Alkyl-N-acetyl-cysteinamides (1) An S-alkyl-N-acetyl-cysteinamide may be prepared by the reaction of an S-alkyl-N-acetylcysteine alkyl ester (II) with an amino compound of formula (III). The amino compound (III) is usually used in excess over the S-alkyl-N-acetylcysteine alkyl ester (II). The reaction is usually carried out in an organic solvent such as methanol or ethanol at a temperature of 0° to 80° C. The reaction time is usually from one hour to several days.

(2) (i) The title compound may also be prepared by the condensation reaction of an S-alkyl-N-acetylcysteine (V) and an amino compound of formula (III). In such cases, a dehydrating condensing agent is normally used and usually N,N′-dicyclohexylcarbodiimide, 1-cyclohexyl-3-(4-diethylaminocyclohexyl)carbodiimide, 1-ethyl-3-(3-diethylaminopropyl)carbodiimide or the like may be used for this purpose. The reaction is usually carried out at room temperature or under cooling in an organic solvent such as dichloromethane or chloroform. The molar ratio of S-alkyl-N-acetylcysteine (V) to amino compound (III) to dehydrating condensing agent is approximately 1:1:1.

(ii) The title compound may be prepared by the reaction of a reactive derivative of an S-alkyl-N-acetylcysteine and an amino compound of formula (III). The reactive derivative of the S-alkyl-N-acetylcysteine includes, for example, mixed acid anhydrides such as alkyl carbonate mixed anhydride, acid chloride and the like. These reactive derivatives need not always be isolated and purified and it is possible to use the reaction mixture in the subsequent reaction with the amino compound (III) as it is. In the reaction, the molar ratio of S-alkyl-N-acetylcysteine to amino compound (III) is usually about 1:1. The reaction is usually carried out at room temperature or under cooling in an organic solvent such as acetone, tetrahydrofuran, dioxane, dimethylformamide, chloroform, dichloromethane or hexamethylphosphoramide, a mixture of two or more of these solvents or a mixture of such organic solvent and water, in the presence of a base such as triethylamine or dimethylaniline.

(3) The title compound may be prepared by reacting an S-alkylcysteine derivative of the formula:

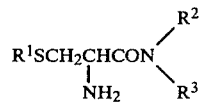

or its salt which is prepared by the reaction of an S-alkylcysteine or its salt or a reactive derivative thereof and an amino compound (III), with acetic acid or its reactive derivative.

The S-alkyl-N-acetyl-cysteinamides as prepared by any of the aforementioned processes may be purified sufficiently in a conventional manner by means of solvent extraction, washing, removal of solvent by distillation, filtration, recrystallization, column chromatography or the like.

Best Mode for Carrying Out the Invention

The following preparations and examples are given to further illustrate the present invention and it is to be understood that they are not intended to restrict the invention in any way.

EXAMPLE 1

To 14.3 g of S-methyl-L-cysteine methyl ester was added 250 ml of methanol saturated with ammonia gas and ammonia gas was further passed through the resulting mixture for 1 hour under ice cooling. After the mixture was allowed to stand at room temperature for 3 days, the solvent and ammonia were distilled off to give 10.9 g of S-methyl-L-cysteinamide as yellow solid.

m.p. 57°–66° C. (Dec.)

IR (cm$^{-1}$) KBr 3,400, 3,200, 3,000, 1,665, 1,320, 1,200

NMR (100 MHz) ppm DMSO-d$_6$ 1.84 (2H, br, s, >CH—N$\underline{H}_2$) 2.05 (3H, s, C$\underline{H}_3$—S—) 2.40–2.82 (2H, AB moiety of ABX type, —S—C$\underline{H}_2$—CH<) 3.20–3.33 (1H, X moiety of ABX type, —S—CH$_2$—C$\underline{H}$<) 7.02 (1H, s, —CON$\underline{H}_2$) 7.36 (1H, s, —CON$\underline{H}_2$)

EXAMPLE 2

S-Methyl-L-cysteinamide (10.9 g) was dissolved in a minimum amount of methanol and hydrogen chloride was passed through the solution. The resulting crystals were collected by filtration, washed with methanol and dried to give 8.0 g of crystalline S-methyl-L-cysteinamide hydrochloride (58% yield).

| | CH$_3$SCH$_2$CHCONH$_2$<br>\|<br>NH$_2$·HCl | | |
|---|---|---|---|
| Elementary analysis (wt. %) | C | H | N |
| Calc. for C$_4$H$_{11}$ON$_2$S: | 28.15 | 6.45 | 16.42 |
| Found: | 28.38 | 6.51 | 16.56 | m.p. 223.0°–223.7° C. (Dec.)

IR (cm$^{-1}$) KBr 3,400, 1,665, 1,320, 1,200

NMR (100 MHz) ppm DMSO-d$_6$ 2.14 (3H, s, C$\underline{H}_3$—S—) 2.97 (2H, br. d, J=6, —S—C$\underline{H}_2$—CH<) 3.92 (1H, t, J=6, —S—CH$_2$C$\underline{H}$<) 7.64 (1H, s, —CON$\underline{H}_2$) 8.19 (1H, s, —CON$\underline{H}_2$) 8.43 (3H, br. s, <CH—N$\underline{H}_2$·HCl)

EXAMPLE 3

S-Methyl-N-t-butyloxycarbonyl-L-cysteine (6.63 g, 28.2 mmole) was dissolved in 70 ml of tetrahydrofuran and 4.18 ml (30 mmole) of triethylamine was added to the solution. To the resulting mixture was added dropwise 3.94 ml (30 mmole) of isobutyl chloroformate under cooling at −15° C. and the mixture was stirred at that temperature for 20 minutes. After cooling to −40° C., 3.9 g (60 mmole) of aqueous 70% ethylamine solution was added in a portion and the mixture was stirred for 3 hours under ice cooling. Thereafter, 30 ml of aqueous 5% sodium bicarbonate was added and the organic layer was separated. The aqueous layer was then extracted with 50 ml of ethyl acetate and the combined organic layers were washed successively with 30 ml of aqueous 5% sodium bicarbonate, 30 ml of aqueous saturated sodium chloride, 30 ml of aqueous 10% citric acid, 30 ml of aqueous 5% sodium bicarbonate and 30 ml of aqueous saturated sodium chloride and dried over anhydrous magnesium sulfate. The solution was then concentrated in vacuo, resulting in formation of crystals, which were collected and recrystallized from ethyl acetate-n-hexane to give 5.17 g of S-methyl-N-butyloxycarbonyl-L-cysteine ethylamide (70% yield), m.p. 106°–7° C.

To 60 ml of ice-cooled 16% solution of hydrogen chloride in ethyl acetate was added dropwise a solution of 3.93 g (15 mmole) of S-methyl-N-butyloxycarbonyl-L-cysteine ethylamide in 60 ml of ethyl acetate over 20 minutes. After stirring for 2 hours, the reaction mixture was concentrated in vacuo and the residual oil was treated with ethyl ether to give 2.8 g (94% yield) of S-methyl-L-cysteine ethylamide hydrochloride as powder.

IR (cm$^{-1}$) KBr 3,420, 3,230, 3,070, 2,980, 1,665, 1,560, 1,490

NMR (100 MHz) ppm DMSO-d$_6$ 1.10 (t, 3H, —CH$_2$C$\underline{H}$$_3$) 2.12 (s, 3H, —SC$\underline{H}$$_3$) 2.94 (d, 2H, —SC$\underline{H}$$_2$CH) 3.0–3.3 (m, 2H, —NHC$\underline{H}$$_2$CH$_3$) 3.90 (t, 1H, CH$_2$C$\underline{H}$CO) 8.3–8.7 (broad, 3H, —N$\underline{H}$$_3$$^+$) 8.95 (t, 1H, CON$\underline{H}$CH$_2$)

EXAMPLE 4

To 14.92 g (100 mmole) of S-methyl-L-cysteine were added 55 ml of water and 21 ml (110 mmole) of triethylamine and the mixture was dissolved in 55 ml of dimethylformamide at room temperature. Thereafter, 26.4 g (110 mmole) of t-butyl-S-4,6-dimethylpyrimidin-2-ylthiol carbanate was added and the mixture was stirred for about 10 hours at room temperature. After addition of 150 ml of water, the mixture was extracted with 2×200 ml of ethyl acetate. The aqueous layer was ice-cooled, adjusted to pH 2 with addition of 6 N hydrochloric acid and extracted with 1×150 ml and 2×80 ml of ethyl acetate. The organic layers were washed with 3×100 ml of 5% hydrochloric acid and 2×100 ml of aqueous saturated sodium chloride and then dried over magnesium sulfate. The solution was concentrated in vacuo to give 24.5 g (98% yield) of S-ethyl-N-butyloxycarbonyl-L-cysteine as an oil.

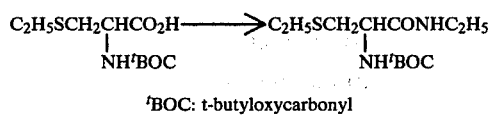

$^t$BOC: t-butyloxycarbonyl

To a solution of 6.23 g (25 mmole) of S-ethyl-N-t-butyloxycarbonyl-L-cysteine dissolved in 60 ml of tetrahydrofuran was added 3.48 ml (25 mmole) of triethylamine. To the resulting mixture cooled to −15° C. was added dropwise 3.28 ml (25 mmole) of isobutyl chloroformate and the mixture was stirred at that temperature for 20 minutes. After cooling to −40° C., 3.2 g of aqueous 70% ethylamine solution (50 mmole) was added in a portion and the mixture was stirred for 2.5 hours under ice cooling. After addition of 70 ml of ethyl acetate, the organic layer was washed successively with 30 ml of aqueous 5% sodium bicarbonate, 2×30 ml of aqueous 10% citric acid, 2×30 ml of aqueous 5% sodium bicarbonate and 2×30 ml of saturated saline and dried over anhydrous magnesium sulfate. The solution was then concentrated in vacuo, resulting in precipitation of crystals, which were recrystallized from ethyl acetate-n-hexane to give 4.93 g of S-ethyl-N-t-butyloxycarbonyl-L-cysteine ethylamide, 71% yield, m.p. 109°–110° C.

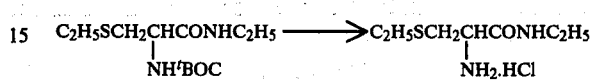

To 40 ml of ice-cooled 16% solution of hydrogen chloride in ethyl acetate was added dropwise a solution of 2.00 g (7.25 mmole) of S-ethyl-N-t-butyloxycarbonyl-L-cysteine ethylamide in 50 ml of ethyl acetate over 20 minutes. After stirring for 2.5 hours at room temperature, the mixture was concentrated in vacuo and the residual oil was treated with ethyl ether to give 1.31 g (85% yield) of S-ethyl-L-cysteine ethylamide hydrochloride as powder.

IR (cm$^{-1}$) KBr 3,420, 3,230, 3,070, 2,970, 1,665, 1,560, 1,490, 1,265

NMR (100 MHz) ppm DMSO-d$_6$ 1.0–1.3 (m, 6H, 2×CH$_3$) 2.59 (q, 2H, CH$_3$CH$_2$S—) 2.8–3.3 (m, 4H, S—CH$_2$CH, —NHCH$_2$CH$_3$) 3.90 (t, 1H, SCH$_2$CH$_3$) 8.3–8.7 (broad, 3H, —NH$_3$$^+$) 8.90 (t, 1H, CONHC$_2$H$_5$)

EXAMPLE 5

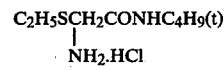

Following the procedure described in Example 4 except that the "aqueous 70% ethylene solution" used in Example 4 was replaced by n-butylamine, S-ethyl-N-t-butyloxycarbonyl-L-cysteine butylamide and subsequently S-ethyl-L-cysteine butylamide hydrochloride were synthesized.

EXAMPLE 6

S-Ethyl-N-t-butyloxycarbonyl-L-cysteine hexylamide and then S-ethyl-L-cysteine hexylamine hydrochloride were synthesized in exactly the same way as in Example 4 except that the "aqueous 70% ethylene solution" used in Example 4 was replaced by n-hexylamine.

EXAMPLE 7

S-Ethyl-N-t-butyloxycarbonyl-L-cysteine methylamide and then S-ethyl-L-cysteine methylamide hydrochloride were synthesized in exactly the same way as in Example 4 except that the "aqueous 70% ethylene solution" used in Example 4 was replaced by an aqueous methylamine solution.

The results of Examples 5 to 7 are summarized in Table 1 below.

TABLE 1-1

| Example | 5 | 6 |
|---|---|---|
| tBOC-Intermediate | S—Ethyl-N—t-butyloxycarbonyl-L-cysteine butylamide | S—Ethyl-N—t-butyloxycarbonyl-L-cysteine hexylamide |
| End product | S—Ethyl-L-cysteine butylamide | S—Ethyl-L-cysteine hexylamide |

TABLE 1-1-continued

| Example | 5 | 6 |
|---|---|---|
| | hydrochloride | hydrochloride |
| Yield, % | 74 | 79 |
| M. P., °C. | 107.8 | 121.7-122.8 |
| IR (cm$^{-1}$) (KBr) | 3,400, 3,200, 2,950, 1,660, 1,560, 1,480, 1,260 | 3,400, 2,930, 1,660, 1,550, 1,260 |
| NMR (100 MHz) ppm | CDCl$_3$<br>0.9 (t, 3H, —CH$_2$CH$_3$)<br>1.2 (broad, t, 3H, CH$_3$CH$_2$S—)<br>1.5 (broad, 4H, NHCH$_2$CH$_2$CH$_2$)<br>2.8 (q, 2H, CH$_3$CH$_2$S—)<br>3.2 (4H, broad, S—CH$_2$CH + NHCH$_2$CH$_2$)<br>4.6 (broad, 1H, SCH$_2$CH—)<br>8.3-8.5 (broad, 4H, —NH$_3$, CONH) | CDCl$_3$<br>0.9 (t, 3H, —CH$_2$CH$_3$)<br>1.1-1.8 (11H, CH$_3$CH$_2$S—, NHCH$_2$CH$_2$CH$_2$CH$_2$CH$_2$CH$_3$)<br>2.7 (q, 2H, CH$_3$CH$_2$S—)<br>3.2 (broad, 4H, SCH$_2$CH + NHCH$_2$)<br>4.5 (broad, 1H, SCH$_2$CH—)<br>7.8-8.4 (broad, 4H, NH$_3$, CONH) |

TABLE 1-2

| Example | 7 |
|---|---|
| tBOC-Intermediate | S—Ethyl-N—t-butyloxycarbonyl-L-cysteine methylamide |
| End product | S—Ethyl-L-cysteine methylamide hydrochloride |
| Yield, % | 79.3 |
| M.P., °C. | 128-132 |
| IR (cm$^{-1}$) (KBr) | 3,450, 3,100, 2,950, 1,680, 1,570, 1,500, 1,420, 1,280 |
| NMR (100 MHz) ppm | DMSO-d$_6$<br>1.2 (t, 3H, CH$_3$CH$_2$S—)<br>2.6 (q, 2H, CH$_3$CH$_2$S—)<br>2.7 (d, 3H, CONHCH$_3$)<br>3.0 (d, 2H, —SCH$_2$CH)<br>3.9 (qui, 1H, —SCH$_2$CH)<br>8.5 (broad, 3H, —NH$_3$)<br>8.9 (q, 1H, CONHCH$_3$) |

EXAMPLE 8

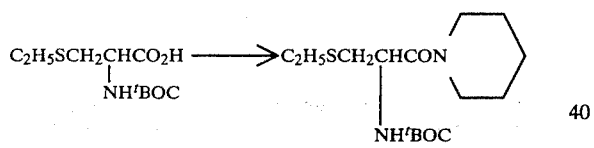

In 50 ml of tetrahydrofuran was dissolved 5.46 g (21.9 mmole) of S-ethyl-N-t-butoxycarbonyl-L-cysteine and 3.05 ml (21.9 mmole) of triethylamine was added thereto. Upon cooling to −15° C., 2.87 ml (21.9 mmole) of isobutyl chloroformate was added dropwise and the mixture was stirred for 20 minutes at that temperature. Upon cooling to −30° C., a solution of 2.79 g (32.9 mmole) of piperidine in 5 ml of tetrahydrofuran was added in one portion and the mixture was stirred for 2.5 hours under ice cooling. After addition of 70 ml of ethyl acetate, the mixture was washed successively with 30 ml of aqueous 5% sodium bicarbonate, 2×30 ml of aqueous 10% citric acid, 2×30 ml of aqueous 5% sodium bicarbonate and 2×30 ml of saturated saline and then dried over anhydrous magnesium sulfate. The resulting solution was concentrated in vacuo to give 6.66 g of S-ethyl-N-t-butyloxycarbonyl-L-cysteine piperidylamide as an oil, 96% yield.

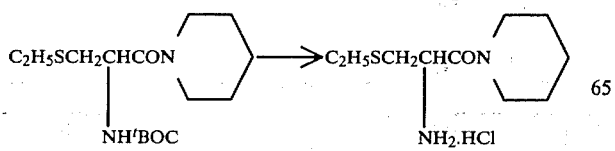

A solution of 6.55 g (20.7 mmole) of S-ethyl-N-t-butyloxycarbonyl-L-cysteine piperidylamide in 100 ml of ethyl acetate was added dropwise over 20 minutes to 80 ml of ice-cooled 16% solution of hydrogen chloride in ethyl acetate. After stirring for 3 hours at room temperature, the reaction mixture was concentrated in vacuo, resulting in the formation of crystals. The crystals were collected, washed with ethyl acetate and then with ethyl ether and dried to give 3.66 g of S-ethyl-L-cysteine piperidylamide hydrochloride, 74% yield.

IR (cm$^{-1}$) KBr 3,420, 2,940, 1,640, 1,475, 1,450, 1,255

NMR (100 MHz) ppm DMSO-d$_6$ 1.16 (t, 3H, CH$_3$CH$_2$S—)

1.2-1.8 (broad, 6H, 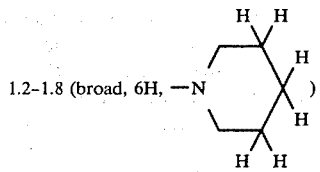)

2.56 (q, 2H, CH$_3$CH$_2$S—)

2.95 (d, 2H, —SCH$_2$CH—)

3.1-3.7 (broad, 4H, 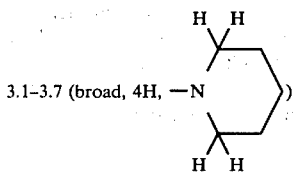)

4.50 (t, 1H, —SCH$_2$CH—)

8.2-8.8 (broad, 3H, —NH$_3^+$)

EXAMPLE 9

S-Ethyl-N-t-butyloxycarbonyl-L-cysteine pyrrolidylamide and then S-ethyl-L-cysteine pyrrolidylamide hydrochloride were synthesized in exactly the same manner as described in Example 8 except that the piperidine used in that example was replaced by pyrrolidine.

Yield of S-ethyl-N-t-butyloxycarbonyl-L-cysteine pyrrolidylamide: 93%.

Yield of S-ethyl-L-cysteine pyrrolidylamide: 75%, m.p. 125.4°-129.6° C.

IR (cm$^{-1}$) KBr 3,400, 2,950, 1,640, 1,480, 1,340, 1,270, 1,150

NMR (100 MHz, CDCl₃) ppm 1.22 (t, 3H, CH₃CH₂S—)

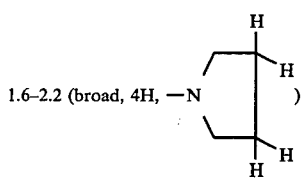

1.6–2.2 (broad, 4H, —N⟨⟩)

2.65 (q, 2H, CH₃CH₂S—)

3.2 (d, 2H, —SCH₂CH—)
              |

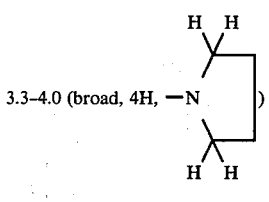

3.3–4.0 (broad, 4H, —N⟨⟩)

4.5 (broad, 1H, —SCH₂CH—)
                    |

8.5 (broad, 3H, —NH₃⁺)

EXAMPLE 10

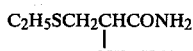
C₂H₅SCH₂CHCONH₂
           |
         NH₂·HCl

Synthesis of S-ethylcysteinamide hydrochloride

In 80 ml of methanol was suspended 4.47 g (0.03 mole) of S-ethylcysteine and 4.28 g (0.036 mole) of thionyl chloride was then added dropwise to the suspension under stirring and ice cooling. The reaction mixture was stirred for about 3 hours and then allowed to stand overnight and the resulting homogenous solution was concentrated. To the residue was added 100 ml of chloroform and the solution was washed with aqueous 5% sodium bicarbonate and dried over anhydrous magnesium sulfate. The chloroform was then distilled off in vacuo to give an oil which is S-ethylcysteinamide. To the oil was added 100 ml of methanol and ammonia gas was passed through the resulting solution under cooling with ice-water until the solution was saturated with ammonia. The solution was then allowed to stand for 2 days as it was. After the methanol and ammonia were distilled off in vacuo, another 80 ml aliquot of methanol was added and hydrogen chloride gas was passed through the resulting solution.

The solution was concentrated and the resulting crystals were collected by filtration and dried to give 1.88 g of S-ethylcysteinamide hydrochloride, 34% yield based on S-ethylcysteine, m.p. 212°–213° C.

IR (cm⁻¹) KBr 3,440, 3,320, 2,980, 1,685, 1,580, 1,485, 1,310, 1,255

NMR (100 MHz) ppm DMSO-d₆ 1.98 (t, 3H, CH₃) 2.60 (q, 2H, CH₃CH₂S—)

2.97 (d, 2H, S—CH₂CH—)
                |

3.90 (t, 1H, S—CH₂CH—CO—)
                   |
                  NH₂

7.6–8.6 (5H, CONH₂+NH₃⁺)

EXAMPLE 11

A homogeneous solution was prepared by adding 175.64 g (1.0 mmole) of L-cysteine monohydrochloride powder to 1 liter of ice-cooled 2 N sodium hydroxide solution (2 mole as NaOH).

To the solution was added 2 l of methyl alcohol and 70 ml (1.10 mole) of methyl iodide was then added dropwise under ice cooling. After white crystals were formed, the mixture was stirred for several hours and then allowed to stand overnight at room temperature. Enough 5% hydrochloric acid was added to adjust to pH 6.5 and the mixture was then ice-cooled and filtered. The collected crystals were washed with aqueous 60% methyl alcohol to give an yield of 62.9 g. The filtrate was concentrated in vacuo to recover a second crop of 69.7 g. Thus, S-methyl-L-cysteine was obtained in a yield of 132.6 g (98% of the theoretical).

S-Methyl-L-cysteine (119.6 g, 0.89 mole) was dissolved in 1.87 l (1.87 mole) of 1 N sodium hydroxide solution and then ice-cooled. Thereafter, 92.6 ml (0.98 mole) of acetic anhydride was added dropwise and the mixture was stirred for 2.0 hours at room temperature. The reaction mixture was acidified to pH 1.0 with 6 N hydrochloric acid and extracted with 1 liter of ethyl acetate five times. The extracts were dried over anhydrous magnesium sulfate and concentrated in vacuo to give 126.4 g of S-methyl-N-acetyl-L-cysteine as an oil (80.6% yield). A second crop of 5.17 g (3.3%) was recovered by reextraction of the aqueous layer.

To 600 ml of methyl alcohol cooled to −10° C. was added dropwise slowly 180 ml (2.54 mole) of thionyl chloride and the mixture was stirred for 20 minutes at −10° C. Thereafter, 131.6 g (0.74 mole) of S-methyl-N-acetyl-L-crysteine was added dropwise at −10° C. and the mixture was stirred for several hours at room temperature and then allowed to stand overnight. The methyl alcohol was distilled off in vacuo and the residue was dissolved in a mixture of 1 liter of chloroform and 1 liter of water. The solution was neutralized by addition of sodium bicarbonate powder and the layers were separated. The aqueous layer was extracted with 1 liter of chloroform twice and the combined chloroform layers were washed successively with 2×600 ml of aqueous 5% sodium bicarbonate and 2×600 ml of aqueous saturated sodium chloride solution, dried over anhydrous magnesium sulfate and concentrated in vacuo to give 130.5 g (92.8% yield) of S-methyl-N-acetyl-L-cysteine methylester as an oil.

In 650 ml of methyl alcohol was dissolved 130.5 g (0.69 mole) of S-methyl-N-acetyl-L-cysteine methylester and the solution was ice cooled. Ammonia gas was then passed through the solution to saturate therewith. The solution was allowed to stand for 3 days at room temperature and then concentrated in vacuo, resulting in the formation of white crystals. The crystals were collected, washed with ethyl ether and dried in vacuo to give 96.5 g (79% yield) of S-methyl-N-acetyl-L-cysteinamide.

m.p. 120.4°–123° C.

[α]_D = −36.6° (1% methyl alcohol solution)

IR (cm$^{-1}$) KBr 3,350, 3,250, 1,680, 1,640, 1,550, 1,410, 1,370, 1,295, 1,180, 1,120, 965, 645, 610, 520, 510

NMR (100 MHz) ppm DMSO-d$_6$ 1.97 (S, 3H, NHCOCH$_3$)

2.07 (S, 3H, CH$_3$S—)

2.70 (m, 2H, —SCH$_2$CH)

4.39 (q, 1H, —SCH$_2$CH)

7.10 and 7.48 (SX2, 2H, CHCONH$_2$)

8.0 (d, 1H, NHCO)

EXAMPLE 12

S-Methyl-DL-cysteine, S-methyl-N-acetyl-DL-cysteine, S-methyl-N-acetyl-DL-cysteine methylester and S-methyl-N-acetyl-DL-cysteinamide were synthesized sequentially in exactly the same manner as described in Example 11 except that the L-cysteine monohydrochloride used in that example was replaced by DL-cysteine monohydrochloride.

m.p. 139.3°–141.7° C.

IR (cm$^{-1}$) KBr 3,250, 3,210, 1,700, 1,679, 1,620, 1,540, 1,420, 1,375, 1,300, 660, 630, 610

NMR (100 MHz) ppm DMSO-d$_6$ 1.84 (s, 3H, NHCOCH$_3$)

2.04 (s, 3H, CH$_3$S—)

2.7 (m, 2H, —SCH$_2$CH)

4.38 (q, 1H, —SCH$_2$CH)

7.07 and 7.44 (SX2, 2H, CHCONH$_2$)

8.0 (d, 1H, NHCOCH$_3$)

EXAMPLE 13

S-Ethyl-N-acetyl-L-cysteinamide was synthesized in exactly the same way as described in Example 11 except that the S-methyl-L-cysteine used in that example was replaced by S-ethyl-L-cysteine.

m.p. 120~(Dec.)

IR (cm$^{-1}$) KBr 3,360, 1,680, 1,620, 1,540, 1,410

NMR (100 MHz) ppm DMSO-d$_6$ 1.17 (t, 3H, CH$_3$CH$_2$S—)

1.86 (s, 3H, NHCOCH$_3$)

2.5 (m, 2H, CH$_3$CH$_2$S—)

2.7 (m, 2H, —SCH$_2$CH)

4.34 (q, 1H, —SCH$_2$CH)

7.1 and 7.5 (sX2, 2H, —CHCONH$_2$)

8.10 (d, 1H, NHCOCH$_3$)

EXAMPLE 14

A solution of 13.5 g (100 mmole) of S-methyl-L-cysteine dissolved in 210 ml of 1 N sodium hydroxide solution was ice cooled and 10.4 ml (110 mmole) of acetic anhydride was added thereto dropwise. After 2.0 hours at room temperature, the mixture was acidified to pH 1.0 with 6 N hydrochloric acid and extracted with ethyl acetate. The extract was dried over anhydrous magnesium sulfate and concentrated in vacuo to give 15.9 g (89.6% yield) of S-methyl-N-acetyl-L-cysteine as an oil.

S-Methyl-N-acetyl-L-cysteine (3.54 g, 20 mmole) was dissolved in 25 ml of tetrahydrofuran and 2.8 ml (20 mmole) of triethylamine was added thereto. Upon cooling to −15° C., 2.7 ml (20 mmole) of butyl chloroformate was added dropwise and the mixture was stirred for 20 minutes at that temperature. After cooling to −40° C., 3.0 ml (46.6 mmole) of aqueous 70% ethylamine solution was added in one portion and stirred for 3 hours under ice cooling. The reaction mixture was extracted with 100 ml of ethyl acetate three times and the extracts were washed successively with 2×30 ml of aqueous 5% sodium bicarbonate and 2×30 ml of saturated saline, dried over anhydrous magnesium sulfate and then concentrated in vacuo. The resulting crystals were collected and washed with ethyl ether to give 2.20 g (53.8% yield) of S-methyl-N-acetyl-L-cysteine ethylamide.

m.p. 104.5°–105.3° C.

IR (cm$^{-1}$) KBr 3,300, 3,240, 3,050, 1,645, 1,580, 1,550, 1,380, 1,265, 1,150, 770, 700, 600

NMR (100 MHz) ppm DMSO-d$_6$ 1.03 (t, 3H, —NHCH$_2$CH$_3$)

1.94 (s, 3H, NHCOCH$_3$)

2.04 (s, 3H, CH$_3$S—)

2.66 (m, 2H, —SCH$_2$CH)

3.08 (qui, 2H, NHCH$_2$CH$_3$)

4.38 (q, 1H, —SCH$_2$CH—)

8.04 (broad, 2H, —CHCONHEt / NHCOCH₃ )

EXAMPLE 15

N-(N-Acetyl-S-methyl-L-cysteinyl)thiazolidine was synthesized in exactly the same manner as described in Example 14 except that the aqueous 70% ethylamine solution used in that example was replaced by thiazolidine.

EXAMPLE 16

S-Ethyl-N-acetyl-L-cysteine ethylamide was synthesized in exactly the same manner as described in Example 14 except that the S-methyl-N-acetyl-L-cysteine used in that example was replaced by S-ethyl-N-acetyl-L-cysteine.

EXAMPLE 17

S-Ethyl-N-acetyl-L-cysteine butylamide was synthesized in exactly the same manner as described in Example 14 except that the S-methyl-N-acetyl-L-cysteine and aqueous 70% ethylamine solution used in that example was replaced by S-ethyl-N-acetyl-L-cysteine and n-butylamine, respectively.

EXAMPLE 18

N-(N-Acetyl-S-ethyl-L-cysteinyl)pyrrolidine was synthesized in exactly the same manner as described in Example 14 except that the S-methyl-N-acetyl-L-cysteine and aqueous 70% ethylamine solution used in that example were replaced by S-ethyl-N-acetyl-L-cysteine and pyrrolidine, respectively.

The results of Examples 15 through 18 are summarized in Table 2 below.

TABLE 2-1

| Example | 15 | 16 |
|---|---|---|
| End product | N—(S—Methyl-N—acetyl-L-cysteinyl)-thiazolidine | S—Ethyl-N—acetyl-L-cysteine ethylamide |
| % Yield | 87 | 47 |
| Melting point, °C. | 98–102 | 104–105 |
| IR (cm⁻¹) KBr | 3,260, 1,660, 1,620, 1,530, 1,440, 1,360, 1,320, 1,280 | 3,270, 3,090, 2,950, 1,640, 1,550, 1,440, 1,370, 1,300, 1,260, 1,150 |
| NMR (100 MHz) ppm | DMSO-d₆<br>1.82 (s, 3H, NHCOCH₃)<br>2.04 (s, 3H, CH₃S—)<br>2.5–2.9 (m, 2H, —N⟨CH₂-CH₂⟩S)<br>3.07 (m, 2H, —SCH₂CH)<br>3.56–3.9 (m, 2H, —N⟨CH₂-CH₂⟩S)<br>4.42 (s, 2H, —N⟨H,H⟩S)<br>4.5–4.8 (m, 1H, —SCH₂CH)<br>8.3 (d, 1H, NHCOCH₃) | CDCl₃<br>1.18 or 1.27 (t, 3H×2 CH₃CH₂S— or CONHCH₂CH₃)<br>2.05 (s, 3H, NHCOCH₃)<br>2.62 (q, 2H, CH₃CH₂S—)<br>2.86 (d, 2H, —SCH₂CH)<br>3.32 (qui, 2H, —NHCH₂CH₃)<br>4.62 (q, 1H, —SCH₂CHCO)<br>7.24 (broad, 2H, —CONHCH₂ and NHCOCH₃) |

L-cysteine.

TABLE 2-2

| Example | 17 | 18 |
|---|---|---|
| End product | S—Ethyl-N—acetyl-N—cysteine butylamide | N—(S—Ethyl-N—acetyl-L-cysteinyl)-pyrrolidine |
| % Yield | 75 | 29 |
| Melting point, °C. | 106.1–106.7 | 100.8–102.6 |
| IR (cm⁻¹) | 3,280, 3,090, 2,950, 2,860, | 3,250, 3,050, 2,950, 2,860, |

TABLE 2-2-continued

| Example | 17 | 18 |
|---|---|---|
| KBr | 1,640, 1,550, 1,440, 1,370, 1,320, 1,300, 1,270, 1,110, 720, 595 | 1,680, 1,620, 1,540, 1,450, 1,360, 1,340, 1,280, 1,180, 1,120 |
| NMR (100 MHz) ppm | CDCl$_3$ 0.96 (t, 3H, —NHC—C—C—CH$_3$) 1.24 (t, 2H, —NHCH$_2$CH$_2$—) 1.36–1.6 (m, 2H, —NHC—C—CH$_2$) 2.0 (s, 3H, NHCOCH$_3$) 2.6 (q, 2H, CH$_3$CH$_2$S—) 2.82 (d, 2H, —SCH$_2$CH—) 3.24 (broad, —NHCH$_2$—C—C—) 4.58 (q, 1H, —SCH$_2$CH—) 7.14 (broad, 2H, —CONH— and NHCOCH$_3$) | CDCl$_3$ 1.26 (t, 3H, CH$_3$CH$_2$S—) 1.8–2.0 (m, 4H, 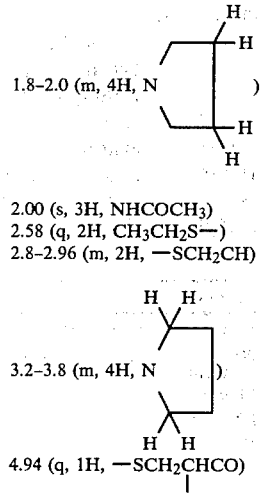) 2.00 (s, 3H, NHCOCH$_3$) 2.58 (q, 2H, CH$_3$CH$_2$S—) 2.8–2.96 (m, 2H, —SCH$_2$CH) 3.2–3.8 (m, 4H, N) 4.94 (q, 1H, —SCH$_2$CHCO) 7.1 (broad, 1H, NHCOCH$_3$) |

EXAMPLE 19

CH$_3$SCH$_2$CHCOOCH$_3$ ⟶ CH$_3$SCH$_2$CHCONHNH$_2$
　　　　|　　　　　　　　　　　　|
　　　NHAc　　　　　　　　　　NHAc

In 20 ml of ethanol were dissolved 1.70 g (8.9 mmole) of S-methyl-N-acetyl-L-cysteine methylester and 6 ml of aqueous 80% hydrazine hydrate solution and the solution was heated at reflux for 2 hours. After the reaction solution was concentrated in vacuo, a small amount of water was added to the residue and then distilled off in vacuo and this procedure was repeated three times to give white crystals. The crystals were washed with small amount of ethanol and dried to give 0.99 g (58% yield) of S-methyl-N-acetyl-cysteinylhydrazine.

IR (cm$^{-1}$) KBr 3,270, 3,050, 1,620, 1,530, 955, 700

NMR (100 MHz) ppm DMSO-d$_6$ 1.84 (s, 3H, CH$_3$S—) 2.04 (s, 3H, —COCH$_3$) 2.4–2.9 (m, 2H, —SCH$_2$CH—) 3.2–4.0 (m, 2H, —NH$_2$)

4.2–4.5 (m, 1H, —CH—)

8.06 (d, 1H, —NHCO—) 9.24 (br, s, 1H, CONHNH$_2$) m.p. 150°–151° C.

EXAMPLE 20

CH$_3$SCH$_2$CHCOOCH$_3$ ⟶ CH$_3$SCH$_2$CHCONHOH
　　　　|　　　　　　　　　　　　|
　　　NHAc　　　　　　　　　　NHAc

The above reaction was carried out in a stream of nitrogen.

A solution of 1.32 g (20 mmole) of potassium hydroxide (85%) in 15 ml of methanol was added dropwise to a solution of 832 mg (12 mmole) of hydroxylamine hydrochloride in 20 ml of methanol under ice cooling sufficient to keep the temperature at +9° to +10° C. Similarly under ice cooling, a solution of 1.91 g (10 mmole) of S-methyl-N-acetyl-L-cysteine methyl ester in 15 ml of methanol was added dropwise. After completion of the dropwise addition, the temperature was allowed to rise to room temperature and the mixture was allowed to stand for 3 days as it was. Thereafter ethyl acetate which contained hydrogen chloride gas was added to attain a pH of about 4. The resulting precipitate was filtered off and the filtrate was concentrated in vacuo by distilling off the methanol. The residue thus obtained was subjected to chromatography on silica gel column (developing solvent: 10% methanol-containing chloroform) to give 1.68 g (88% yield) of N-(S-methyl-N-acetylcysteinyl)-hydroxylamine.

m.p. 126.3°–127.2° C.

IR (cm$^{-1}$) KBr 3,340, 3,230, 2,900, 1,660, 1,605, 1,540

NMR (100 MHz) ppm DMSO-d$_6$ 1.85 (s, 3H, CH$_3$S—) 2.08 (s, 3H, —COCH$_3$) 2.4–2.9 (m, 2H, —SCH$_2$CH)

4.1–4.5 (m, 1H, CH—)

8.08 (d, 1H, —NHCO—) 8.82, 10.68 (br, S, 2H, CONHOH)

EXAMPLE 21

In 20 ml of ethyl alcohol was dissolved 1.91 g (10 mmole) of S-methyl-N-acetyl-L-cysteine methylester and 5.4 ml (100 mmole) of methylhydrazine was added. The mixture was stirred for 3 hours at boiling temperature and then allowed to stand for 1 day at room temperature. After the precipitate was removed, the ethyl alcohol and the excess methylhydrazine were distilled off in vacuo to leave crystals. Thus, 1.05 g (5.1 mmole) of N-methyl-N-(S-methyl-N-acetylcysteinyl)-hydrazine was obtained in 51% yield.

m.p. 156.1°–157.3° C.

IR (cm$^{-1}$) KBr 3,290, 3,040, 2,980, 2,970, 2,930, 1,640, 1,535, 1,500, 1,445, 1,418, 1,385, 1,370, 1,318, 1,280, 1,260, 1,200, 1,110, 1,090, 1,040, 1,020, 1,000, 970, 940, 880, 780, 740, 710, 680, 610, 600, 530, 500 NMR (100 MHz) ppm DMSO-d$_6$ 1.84 (s, 3H, NHCOCH$_3$)

2.05 (s, 3H, C$\underline{H}_3$SCH$_2$) 2.42 (s, 3H, —N(C$\underline{H}_3$)NH$_2$) 2.64 (m, 2H, —SC$\underline{H}_2$CH—) 4.32 (q, 1H, —SCH$_2$C$\underline{H}$—) 4.74 and 9.48 (b.S, 2H, —N(—CH$_3$)N$\underline{H}_2$)

8.04 (d, 1H, NHCOCH$_3$)

Test I (1) Effect on acceleration of growth of liver cells in mice:

Prior to cell division the genes are divided and the synthesis of DNA which comprises the major portion of the genes are concomitantly accelerated.

Such acceleration of DNA synthesis can be determined quantitatively with good reproducibility by using isotopic carbon-containing thymidine as a label.

Thus, the animals used are mice weighing 19 to 24 g and 1 microcurie of $^{14}$C thymidine (5.0–50.7 curie/mol) is intraperitoneally applied to each animal. After 1.5 hours, the mice are killed and the livers are immediately excised. The DNA fractions are then extracted according to the method known per se and the radioactivity of the DNA is determined with a liquid scintillation counter after mixing with 0.6% 2,5-diphenyloxazole solution (in toluene solvent).

The test compound is administered intraperitoneally to the mice 24 hours before the killing. The results are shown in Table 3.

TABLE 3

| Test compound 0.1 mg dose, i.p. | Radioactivity of $^{14}$C—thymidine incorporated into DNA dpm/mg DNA |
|---|---|
| S—Methyl-L-cysteinamide hydrochloride | 2,888 (236%) |
| Glycyl-histidyl-lysine acetate 3 ½ hydrate* | 1,574 (129%) |
| Control (0.1 ml of aqueous 0.9% sodium chloride) | 1,222 (100%) |

*Note: This compound is reported to have a powerful growth accelerating effect on liver cells and a life prolonging effect.

[see Picard, L. and Thaler, M. M., Nature New Biology, 234, 85–7 (1973) U.K., and Picard, L. and thaler, M. M., Experientia, 33, 324–5 (1977)] In addition, the accelerating effect of S-methylcysteinamide on liver DNA synthesis in mice was tested with time. The experimental procedure was the same as described above except that 0.2 mg of the test compound is applied intraperitoneally to mice 18, 24, 32, 37 and 42 hours before the killing. The results are summarized in Table 4.

TABLE 4

| Time interval between 0.2 mg i.p. administration of test compound and killing | Radioactivity of $^{14}$C—thymidine incorporated into DNA dpm/mg DNA |
|---|---|
| 18 hr. | 4.39 |
| 24 | 5.91 |
| 32 | 3.94 |
| 37 | 3.72 |
| 42 | 3.36 |
| Control (0.2 ml of aqueous 0.9% sodium chloride) 24 | 1.58 |

Test II (1) Effect on acute hepatic failure accompanied by centrolobular necrosis (Hepatitis model in single application of carbon tetrachloride)

The administered carbon tetrachloride undergoes metabolism with the aid of chemical metabolizing enzymes in the liver microsomes to form the trichlororadical. This radical injures liver cell membranes, mitochondria membranes or membranes of the microsomes, thereby losing the liver cells their inherent functions and inducing centrolobular necrosis. Simultaneously with such injury of liver cells, release of enzymes also takes place and various enzymatic activities appear in the serum. Accordingly, it is reasonable to determine the activity of serum transaminase as an index of such injury. The serum transaminase includes both GOT (glutamate-oxalacetate transaminase) and GPT (glutamate-pyruvate transaminase) and both of these enzymatic activities are determined.

Test Method

The test compound is dissolved in water or suspended therein along with polyoxyethylene sorbitan monooleate (available from Kao-Atlas under the trademark "Tween 80") and orally administered to rats weighing 100 to 150 g at doses of 125, 250 and 500 mg/kg. After 3 hours, carbon tetrachloride was applied intraperitoneally at a dose of 0.25 ml/kg. After 24 hours, the rats are killed and blood samples are collected and subjected to centrifugal sedimentation to collect the plasmas. The GOT and GPT activities are assayed and expressed in terms of the international unit. The results are summarized in Table 5.

TABLE 5

| | 250 mg/kg dose of test compound | | | |
|---|---|---|---|---|
| Measured parameter | Apply CCl$_4$ | Control | S—Methyl-L-cysteinamide hydrochloride 250 mg/Kg | Isothioprolan 250 mg/Kg |
| G O T | 293 ± 43 | 64 ± 16 | 115 ± 9.0 | 81 ± 4.1 |
| G P T | 70 ± 14 | 5.0 ± 1.0 | 18 ± 3.5 | 12 ± 1.4 |

Carbon tetrachloride is a chemical suitable as a symptomatic model for acute hepatitis in test animals. As a result of the experiments as above, the compounds according to this invention exhibited significant preventive effect on experimental hepatopathy as shown above. This effect was comparable to that of isothioprolan.

are expressed according to the international unit expression. The results are summarized in Table 7.

TABLE 7

| Measured parameter | Control | Application of CCl₄ alone | Activity | | | | | |
|---|---|---|---|---|---|---|---|---|
| | | | Medication with S—methyl-N—acetyl-L-cysteinamide | | | Medication with thiola (α-mecoptopropionylglycine) | | |
| | | | 31 mg/Kg | 62 mg/Kg | 125 mg/Kg | 31 mg/Kg | 62 mg/Kg | 125 mg/Kg |
| G P T (I U) | 10 ± 3.2 | 103 ± 10 | 106 ± 19 | 71 ± 2.5 | 47 ± 6.1 | — | 152 ± 49 | 157 ± 28 |
| G O T (I U) | 45 ± 6.5 | 582 ± 57 | 526 ± 45 | 426 ± 39 | 299 ± 38 | — | 654 ± 45 | 1,063 ± 135 |

Test Method

The test compound is dissolved in water or suspended therein along with polyoxyethylene sorbitan monooleate (available from Kao-Atlas under the trademark "Tween 80") and orally administered to rats weighing 100 to 150 g at doses of 125 mg/kg. After 3 hours carbon tetrachloride was applied intraperitoneally at a dose of 0.25 ml/kg, and after another 3 hours 125 mg/kg of the test compound is again administered orally. After 24 hours, the rats are killed and blood samples are collected and subjected to centrifugal sedimentation to collect the serums. The GOT and GPT activities are assayed and expressed in terms of the international unit. The reults are summarized in Table 6.

TABLE 6

| Liver injuring agent | Measured parameter | Activity (IU) | | | | |
|---|---|---|---|---|---|---|
| | | Control | Application of CCl₄ alone | Compound of Ex. 10 | Compound of Ex. 4 | Methionine |
| Carbon tetrachloride | G O T | 64 ± 16 | 293 ± 43 | 195 ± 34 | 120 ± 7.4 | 350 ± 79 |
| | G P T | 5.0 ± 1.0 | 70 ± 14 | 33 ± 7.8 | 57 ± 24 | 82 ± 20 |

Carbon tetrachloride is a chemical suitable as a symptomatic model for acute hepatitis in test animals. As a result of the experiments as above, the compounds according to this invention exhibited significant preventive effect on experimental hepatopathy as shown above. This effect was more powerful than that of methionine which are conventionally employed as a therapeutic agent for hepatopathy.

Test Method

The test compound is orally administered to rats (male wister weighing around 100 g) at doses of 31, 62 and 125 mg/kg and 3 hours later carbon tetrachloride is applied intraperitoneally at a dose of 0.25 ml/kg (after dilution with 3 volumes of olive oil). After an additional 24 hours, the rats are killed and blood samples are collected from the great abdominal veins and subjected to centrifugal sedimentation to collect the serums. The serum GOT and GPT are assayed and their activities The test compound, S-methyl-N-acetyl-L-cysteinamide exerted its beneficial effect superior to that of thiola (α-mercaptopropionylglycine) as a control drug.

Test Method

The test compound is orally administered to rats (male wister weighing around 100 g) at doses of 125 mg/kg and 3 hours later carbon tetrachoride is applied intraperitoneally at a dose of 0.25 ml/kg (after dilution with 3 volumes of olive oil). Further 24 hours later the rats are killed and blood samples are collected from the great abdominal veins and subjected to centrifugal sedimentation (10 minutes at 3,000 rpm) to collect the serums. The serum GOT and GPT are assayed and their activities are expressed according to the international unit system. The results are summarized in Table 8.

TABLE 8

| Measured parameter | Activities | | | | | |
|---|---|---|---|---|---|---|
| | Control | Application of CCl₄ alone | Compound of Ex. 19 125 mg/Kg | Compound of Ex. 20 125 mg/Kg | Compound of Ex. 21 125 mg/Kg | α-Mercaptopropionylglycine 125 mg/Kg |
| G P T (IU) | 10 ± 3.2 | 157 ± 23 | 47 ± 13 | 61 ± 10 | 97 ± 10 | 166 ± 43 |
| Number of animals | 4 | 13 | 5 | 5 | 5 | 5 |

The test compound exerted its beneficial effect superior to that of the control drug, α-mercaptopropionylglycine and suppressed the carbon tetrachloride-induced lesion at a dose of 125 mg/kg.

(2) Effect on acute hepatitis accompanied by interlobar reaction and sporadolobular necrosis (Model test by single application of D-galactosamine)

When D-galactosamine is applied in a large dose, UDP-glucose (uridine diphosphate-glucose) which is normally to be synthesized in the liver undergoes a competitive inhibition due to the D-galactosamine and the amount thereof is decreased. On this account, the synthesis of glycogen and glucuronide which goes through the UDP-glucose is suppressed to induce a functional failure of liver cells. The symptomatic organ picture causes a sporadic necrosis accompanied by an interlobar reaction which resembles viral hepatitis in human being.

Test Method

The test compound is dissolved in water or suspended therein along with polyoxyethylene sorbitan monooleate (as described above) and orally administered to rats weighing 200 to 250 g at doses of 125 to 1,000 mg/kg. After 3 hours, D-galactosamine was applied intraperitoneally at a dose of 400 mg/kg. After an additional 2 hours, the test compound is again administered at a dose of 125 mg/kg. After 22 hours, the rats are killed and blood samples are collected and subjected to centrifugal sedimentation to collect the plasmas. The GOT and GPT activities are assayed and expressed in terms of the international unit. The results are summarized in Table 11.

TABLE 11

| Liver injuring agent | Measured parameter | Control | Application of liver injuring agent alone | Compound of Ex. 7 | Compound of Ex. 1 | Methionine | Diisopropyl-1,3-dithiol-2-ylidene malonate (isothioprolan) |
|---|---|---|---|---|---|---|---|
| D-galactosamine | GOT | 67 ± 16 | 1,184 ± 506 | 225 ± 51 | 245 ± 45 | 588 ± 258 | 210 ± 100 |
|  | GPT | 18 ± 0.87 | 580 ± 279 | 130 ± 36 | 72 ± 14 | 290 ± 94 | 89 ± 59 | plied intraperitoneally at a dose of 400 mg/kg. After an additional 2 hours, the test compound was again administered at doses of 125 to 1,000 mg/kg. After 22 hours, the rats are killed and blood samples are collected and subjected to centrifugal sedimentation to collect the plasmas. The GOT and GPT activities are assayed and expressed in terms of the international unit. The results are summarized in Tables 9 and 10.

As shown above, the compound of this invention exhibited a significant preventive effect on liver disorder and its effect is superior to that of methionine presently commercially available as a liver medicine and is comparable to that of isothioprolan.

Test Method

The test compound, S-methyl-N-acetyl-L-cysteinamide, and thiola are orally administered to rats (male wister weighing around 200 g) at doses of 31, 62 and 125 mg/kg and 3 hours later D-galactosamine is applied intraperitoneally at a dose of 400 mg/kg. Further 24 hours later the rats are killed and blood samples are collected from the great abdominal veins and subjected to centrifugal sedimentation to collect the serums. The serum GOT and GPT are assayed and their activities are expressed according to the international unit system. The results are summarized in Table 12.

TABLE 9

| | 1 g/kg dose of test compound | | | | |
|---|---|---|---|---|---|
| Measured parameter | Control | Apply D-galactosamine alone | S—Methyl-L-cysteinamide hydrochloride | N—Acetyl-cysteine | Cysteine |
| GOT | 47 ± 4.6 | 249 ± 203 | 57 ± 5.2 | 788 ± 310 | 280 ± 145 |
| GPT | 8.2 ± 0.8 | 51 ± 15 | 9.3 ± 1.6 | 221 ± 96 | 156 ± 93 |

TABLE 10

| | | | 125–500 mg/kg doses of test compound | | | | | |
|---|---|---|---|---|---|---|---|---|
| Measured parameter | Control | Apply D-galactos-amine | S—Methyl-L-cysteinamide hydrochloride 500 mg/Kg | S—Methyl-L-cysteinamide hydrochloride 250 mg/Kg | S—Methyl-L-cysteinamide hydrochloride 125 mg/Kg | Iso-thioprolan 500 mg/Kg | Isothioprolan 250 mg/Kg | Methionine 500 mg/Kg | Glutathione 250 mg/Kg |
| GOT | 58 ± 7.4 | 515 ± 79 | 228 ± 52 | 168 ± 47 | 240 ± 52 | 224 ± 23 | 200 ± 32 | 299 ± 53 | 196 ± 42 |
| GPT | 18 ± 4.4 | 98 ± 22 | 41 ± 40 | 27 ± 6.3 | 48 ± 13 | 42 ± 8.0 | 62 ± 17 | 57 ± 18 | 28 ± 7.8 |

As shown above, the compound according to this invention exhibited a significant preventive effect on liver disorder and its effect is comparable to those of methionine, glutathione, N-acetylcysteine and cysteine which are at present commercially available as liver drugs and that of isothioprolan which is a compound described in a patent.

Test Method

The test compound is dissolved in water or suspended therein along with polyoxyethylene sorbitan monooleate (as aforementioned) and orally administered to rats weighing 200 to 250 g at a dose of 125 mg/kg. After 3 hours, D-galactosamine was applied intraperitoneally at a dose of 125 ml/kg. After an additional 2 hours, the test compound is again administered at a dose of 125 mg/kg. After 22 hours, the rats are killed and blood samples are collected and subjected to centrifugal sedimentation to collect the plasmas. The GOT and GPT activities are assayed and expressed in terms of the international unit. The results are summarized in Table 11.

TABLE 12

| | | | Activity | | | | | |
|---|---|---|---|---|---|---|---|---|
| Measured parameter | Control | Application of D-galactosamine alone | Medication with S—methyl-N—acetyl-L-cysteinamide | | | Medication with thiola | | |
| | | | 31 mg/Kg | 62 mg/Kg | 125 mg/Kg | 125 mg/Kg | 250 mg/Kg | 500 mg/Kg |
| GPT (IU) | 10 ± 1 | 217 ± 95 | 137 ± 26 | 108 ± 23 | 95 ± 26 | 280 ± 95 | 313 ± 26 | 188 ± 13 |
| GOT (IU) | 50 ± 2.0 | 759 ± 347 | 456 ± 83 | 494 ± 79 | 290 ± 25 | 845 ± 256 | 1,078 ± 564 | 978 ± 571 |

The beneficial effect of the test compound, S-methyl-N-acetyl-L-cysteinamide is superior to that of the commercially available liver medicine, thiola, which is used as a control.

Test Method

The test compound (CH$_3$SCH$_2$CHCONHNH$_2$,
                                           |
                                        NHCOCH$_3$ S-methyl-N-acetyl-cysteinylhydrazine) and NKK 100 (diisopropyl 1,3-dithiolan-2-ylidenemalonate, manufactured by Nihon Noyaku Co., Ltd.) are each administered orally to rats (male wister weighing around 200 g) at doses of 62 and 125 mg/kg and 3 hours later D-galactosamine is applied intraperitoneally at a dose of 400 mg/kg. After an additional 24 hours, the rats are killed and blood samples are collected from the great abdominal veins and subjected to centrifugal treatment to collect the serums. The serum GOT and GPT are assayed and their activities are expressed according to the international unit system. The results are summarized in Table 13.

TABLE 13

| | Measured parameter | Run 1 125 mg/Kg dose | Run 2 62.5 mg/Kg dose |
|---|---|---|---|
| Control | G O T (I U) | | 51 ± 6 (3) |
| | G P T (I U) | 11 ± 3.5 (4) | 10 ± 4 (3) |
| Application with D-galactosamine alone | G O T G P T | 57.8 ± 8.1 (9) | 272 ± 37 (7) 94.6 ± 19 (7) |
| Medication with S—methyl-N—acetyl cysteinylhydrazine | G O T G P T | 27.3 ± 4.4 (6) | 180 ± 40 (6) 57.3 ± 12.0 (5) |
| Medication with control drug | G O T G P T | 32.2 ± 7.2 (6) | 165 ± 23 (6) 54.7 ± 16.2 (6) |

The figures in the parentheses represent the number of rats.

The test compound (S-methyl-N-acetylcysteinylhydrazine) has a beneficial effect almost equivalent to that of NKK 100 (diisopropyl 1,3-dithiolan-2-ylidenemalonate) used as a control drug.

Test Method

The test compounds, S-ethyl-N-acetylcysteine ethylamide and S-methyl-N-acetylcysteine ethylamide are each orally administered to rats (male wister weighing around 200 g) at a dose of 125 mg/kg and 3 hours later D-galactosamine is applied intraperitoneally at a dose of 400 mg/kg. After an additional 24 hours, the rats are killed and blood samples are collected from the great abdominal veins and subjected to centrifugal sedimentation to collect the serums. The serum GOT and GPT are assayed and their activities are expressed according to the international unit system. The results are summarized in Table 14.

TABLE 14

| Group | Measured parameter | Run 1 S—Ethyl-N— acetylcystein ethylamide 125 mg/Kg | Run 2 S—Methyl-N— acetylcysteine ethylamide 125 mg/Kg |
|---|---|---|---|
| Control | G O T (I U) | 47 ± 4.7 | 67 ± 16 |
| | G P T (I U) | 8 ± 2.0 | 18 ± 0.9 |
| Application of D-galactosamine (I U) alone | G O T | 987 ± 367 | 487 ± 123 |
| | G P T (I U) | 440 ± 199 | 146 ± 44 |
| Medication with test compound | G O T (I U) | 355 ± 118 | 326 ± 43 |
| | G P T (I U) | 116 ± 59 | 92 ± 13 |
| Medication with methionine | G O T (I U) | 785 ± 139 | |
| | G P T (I U) | 363 ± 95 | |

Both of the test compounds significantly prevent acute D-galactosamine hepatitis.

(3) Liver protective action against acute acetaminophenone hepatopathy

Acetaminophenone which is generally applied to human as an antipyretic may induce an acute hepatopathy upon excess administration thereof and this becomes a clinical problem. This is explained to be caused by the toxicity of a metabolite of acetaminophenone or decrease of reduced-type glutathione in the liver.

It has been proved that acetaminophenone also induces a similar hepatopathy in mice and such drug that exhibit a high hepatopathy preventive and therapeutic effect in this experimental model is also effective for human in prevention and treatment of acute acetaminophenone toxicosis or acute hepatopathy induced by another chemical.

Test Method

The test compound is orally administered to mice (ddy male weighing around 20 g) at doses of 50 to 400 mg/kg and 2 hours and 30 minutes later 500 mg/kg of acetaminophenone dissolved in physiological saline is applied intraperitoneally. After 24 hours, the number of dead mice is counted. The mice which remain alive are killed and blood samples are collected. The activities of GPT are determined and expressed according to the international unit system. The results are summarized in Table 15.

TABLE 15

| Group | Dose mg/Kg | Run 1 Death rate | Run 1 G P T (I U) | Run 2 Death rate | Run 2 G P T (I U) |
|---|---|---|---|---|---|
| Control | | 0/5 | 10 ± 1 | | |
| Application of acetaminophenone alone | | 0/10 | 1,235 ± 256 | 1/8 | 781 ± 271 |
| Medication with S—methyl-N—acetyl- L-cysteinamide | 50 | 1/6 | 1,068 ± 171 | 1/6 | 1,037 ± 156 |
| | 100 | 0/6 | 1,118 ± 264 | 4/6 | 586 ± 330 |
| | 200 | 0/6 | 172 ± 78 | | |
| Medication with thiola | 50 | 4/6 | 1,907 ± 429 | | |
| | 100 | 1/6 | 841 ± 169 | | |
| | 200 | 2/4 | 2,077 ± 253 | 3/6 | 1,028 ± 486 |
| | 400 | | | 0/6 | 1,619 ± 493 |

TABLE 15-continued

| Group | Dose mg/Kg | Run 1 Death rate | Run 1 GPT (IU) | Run 2 Death rate | Run 2 GPT (IU) |
|---|---|---|---|---|---|
| Medication with cysteine | 50 | 3/6 | 558 ± 375 | | |
| | 100 | 1/6 | 567 ± 221 | | |
| | 200 | | | 1/6 | 649 ± 352 |
| | 400 | | | 0/6 | 687 ± 346 |
| Medication with glutathione | 400 | | | 1/6 | 929 ± 523 |

The test compound, S-methyl-N-acetyl-L-cysteinamide exhibits a beneficial effect almost comparative to or higher than that of cysteine which is a control drug and apparently higher than those of thiola and glutathione. Therefore, the test compound, S-methyl-N-acetyl-L-cysteinamide is useful as detoxicating and therapeutic agent in hepatopathy induced by excess administration of acetaminophenone or by another toxic chemical.

Industrial Applicability:

The compounds according to this invention are expected to be applicable as therapeutic agents for hepatic failures.

We claim:

1. A method for accelerating regeneration of parenchymatous cells of the human or animal liver, when the number or function of said cells is reduced due to hepatic failure due to various hepatopathy inducing factors such as acute and chronic hepatitis or chemical poisoning, which comprises orally or parenterally administering to said human or animal a therapeutically effective amount of a cysteine derivative having the formula:

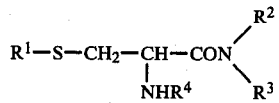

wherein $R_1$ is methyl or ethyl, $R_2$ and $R_3$ are each hydrogen or a lower alkyl having about 1-6 carbon atoms, and $R_4$ is acetyl, or a non-toxic pharmaceutically acceptable acid addition salt thereof.

2. A method as claimed in claim 1, wherein said therapeutically effective amount is 0.1-500 mg/kg-body weight/day for animals.

3. A method as claimed in claim 1, wherein said therapeutically effective amount is 0.1-250 mg/kg-body weight/day for humans.

* * * * *